United States Patent
Jonas et al.

(10) Patent No.: US 6,495,557 B1
(45) Date of Patent: Dec. 17, 2002

(54) CONDENSED THIENOPYRIMIDINES WITH PHOSPHODIESTERASE-V INHIBITING ACTION

(75) Inventors: Rochus Jonas, Darmstadt (DE); Pierre Schelling, Mühltal (DE); Franz-Werner Kluxen, Darmstadt (DE); Maria Christadler, Rödermark (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/674,269

(22) PCT Filed: Apr. 23, 1999

(86) PCT No.: PCT/EP99/02738

§ 371 (c)(1),
(2), (4) Date: Mar. 23, 2001

(87) PCT Pub. No.: WO99/55708

PCT Pub. Date: Nov. 4, 1999

(30) Foreign Application Priority Data

Apr. 29, 1998 (DE) ............................ 198 19 023

(51) Int. Cl.⁷ ................ A61K 31/505; C07D 491/00
(52) U.S. Cl. ........................................ 514/267; 544/250
(58) Field of Search ........................... 514/267; 544/250

(56) References Cited

FOREIGN PATENT DOCUMENTS

| EP | 579496 | 1/1994 |
|----|--------|--------|
| EP | 640599 | 1/1994 |
| EP | 728759 | 8/1996 |
| WO | WO 9422855 | 10/1994 |
| WO | WO 9428902 | 12/1994 |
| WO | WO 9806722 | 2/1998 |
| WO | WO 9817668 | 4/1998 |
| WO | WO 9928325 | 6/1999 |

*Primary Examiner*—Mukund J. Shah
*Assistant Examiner*—Tamthom N. Truong
(74) *Attorney, Agent, or Firm*—Millen, White, Zelano & Branigan, P.C.

(57) ABSTRACT

Thienopyrimidines of the formula I

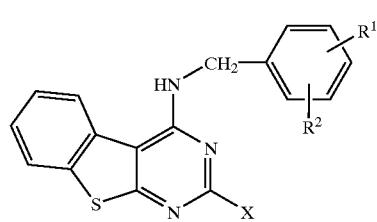

and their physiologically acceptable salts, in which $R^1$, $R^2$ and X have the meanings given in claim 1, inhibit phosphodiesterase V and can be employed for the treatment of illnesses of the cardiovascular system and for the treatment and/or therapy of impaired potency.

18 Claims, No Drawings

CONDENSED THIENOPYRIMIDINES WITH PHOSPHODIESTERASE-V INHIBITING ACTION

The invention relates to compounds of the formula I

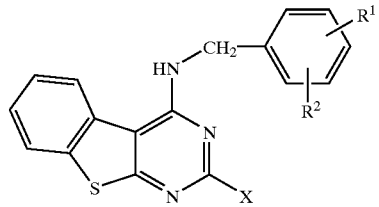

in which
- $R^1$, $R^2$ independently of one another are each H, A, OA or Hal,
- $R^1$ and $R^2$ together are also alkylene having 3–5 carbon atoms, —O—CH$_2$—CH$_2$—, —CH$_2$—O—CH$_2$—, —O—CH$_2$—O— or —O—CH$_2$—CH$_2$—O—,
- X is $R^5$, $R^6$ or $R^4$ which is monosubstituted by $R^7$,
- $R^4$ is linear or branched alkylene having 1–10 carbon atoms, in which one or two CH$_2$ groups may be replaced by —CH=CH— groups,
- $R^5$ is cycloalkyl or cycloalkylalkylene having 5–12 carbon atoms,
- $R^6$ is phenyl or phenylmethyl,
- $R^7$ is COOH, COCA, CONH$_2$, CONHA, CON(A)$_2$ or CN,
- A is alkyl having 1 to 6 carbon atoms and
- Hal is F, Cl, Br or I, and their physiologically acceptable salts.

Pyrimidine derivatives are known, for example, from EP 201 188 or WO 93/06104.

The invention was based on the object of discovering new compounds having valuable properties, in particular those which can be used for the preparation of medicaments.

It has been found that the compounds of the formula I and their salts have very valuable The compounds of the formula I can be employed as medicament active compounds in human and veterinary medicine. They can furthermore be employed as intermediates for the preparation of further medicament active compounds.

The invention accordingly provides the compounds of the formula I and a process for the preparation of compounds of the formula I according to claim 1, and of their salts, characterized in that a) a compound of the formula II

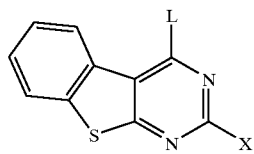

in which
X is as defined above
and L is Cl, Br, OH, SCH$_3$ or a reactive esterified OH group is reacted with a compound of the formula III

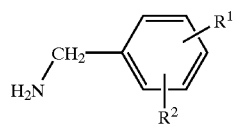

in which
$R^1$ and $R^2$ are as defined above,
or b) a radical X in a compound of the formula I is converted into another radical X, for example by hydrolysing an ester group to a COOH group or converting a COOH group into an amide or a cyano group and/or in that a compound of the formula I is converted into one of its salts.

Above and below, the radicals $R^1$, $R^2$, $R^3$, $R^4$, $R^5$, $R^6$, $R^7$, X and L have the meanings given for the formulae I, II and III, unless expressly stated otherwise.

A is alkyl having 1–6 carbon atoms. In the above formulae, alkyl is preferably unbranched and has 1, 2, 3, 4, 5, or 6 carbon atoms, and is preferably methyl, ethyl or propyl, furthermore preferably isopropyl, butyl, isobutyl, sec-butyl or tert-butyl, but also n-pentyl, neopentyl, isopentyl or hexyl.

X is an $R^4$-, $R^5$- or $R^6$-radical which is monosubstituted by $R^7$.

$R^4$ is a linear or branched alkylene radical having 1–10 carbon atoms, where the alkylene radical is preferably, for example, methylene, ethylene, propylene, isopropylene, butylene, isobutylene, secbutylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, linear or branched heptylene, octylene, nonylene or decylene.

$R^5$ is furthermore, for example, but-2-enylene or hex-3-enylene.

Very particular preference is given to ethylene, propylene or butylene.

$R^5$ is cycloalkylalkylene having 5–12 carbon atoms, preferably, for example, cyclopentylmethylene, cyclohexylmethylene, cyclohexylethylene, cyclohexylpropylene or cyclohexylbutylene. $R^5$ is also cycloalkyl preferably having 5–7 carbon atoms. Cycloalkyl is, for example, cyclopentyl, cyclohexyl or cycloheptyl.

Hal is preferably F, Cl or Br, but also I.

The radicals $R^1$ and $R^2$ may be identical or different and are preferably in the 3- or 4-position of the phenyl ring. Independently of one another they are in each case, for example, H, alkyl, F, Cl, Br or I, or together they are alkylene, such as, for example, propylene, butylene or pentylene, furthermore ethyleneoxy, methylenedioxy or ethylenedioxy. Preferably, they are also in each case alkoxy, such as, for example, methoxy, ethoxy or propoxy.

The radical $R^7$ is preferably, for example, COOH, COOCH$_3$, COOC$_2$H$_5$, CONH$_2$, CON(CH$_3$)$_2$, CONHCH$_3$ or CN.

For the entire invention, all the radicals which occur several times can be identical or different, that is to say independent of one another.

The invention accordingly particularly provides those compounds of the formula I in which at least one of the radicals mentioned has one of the abovementioned preferred meanings. Some preferred groups of compounds can be expressed by the following part formulae Ia to Id, which correspond to the formula I and wherein the radicals not defined in more detail have the meaning given for the formula I, but in which in Ia X is phenyl, phenylmethyl or $R^4$ which is substituted by COOH, COOA, $CONH_2$, $CONA_2$, CONHA or CN;

in Ib $R^1$ and $R^2$ together are alkylene having 3–5 carbon atoms, —O—$CH_2$—$CH_2$—, —O—$CH_2$—O— or —O—$CH_2$—$CH_2$—O, X is phenyl, phenylmethyl or $R^4$ which is substituted by COOH, COOA, $CONH_2$, $CONA_2$, CONHA or CN;

in Ic $R^1$, $R^2$ independently of one another are in each case H, A, OA or Hal, $R^1$ and $R^2$ together are alkylene having 3–5 carbon atoms, —O—$CH_2$—$CH_2$—, —O—$CH_2$—O— or —O—$CH_2$—$CH_2$—O, X is phenyl, phenylmethyl or $R^4$ which is substituted by COOH, COOA, $CONH_2$, $CONA_2$, CONHA or CN;

in Id $R^1$, $R^2$ independently of one another are in each case H, A, OA or Hal, $R^1$ and $R^2$ together are also alkylene having 3–5 carbon atoms, —O—$CH_2$—$CH_2$—, —O—$CH_2$—O— or —O—$CH_2$—$CH_2$—O—, X is cyclohexyl, phenyl, phenylmethyl or alkylene having 2–5 carbon atoms which is monosubstituted by $R^7$, $R^7$ is COOH or COOA, A is alkyl having 1 to 6 carbon atoms, Hal is F, Cl, Br or I.

The compounds of the formula I and also the starting materials for their preparation are otherwise prepared by methods known per se, such as are described in the literature (for example in the standard works, such as Houben-Weyl, Methoden der organischen Chemie [Methods of organic chemistry], Georg-Thieme-Verlag, Stuttgart), and in particular under reaction conditions which are known and suitable for the reactions mentioned. For these reactions, it is also possible to utilize variants which are known per. se and are not mentioned here in more detail.

In the compounds of the formulae II and III, $R^1$, $R^2$, $R^3$, $R^4$, X and n have the meanings given, in particular the preferred meanings given.

If L is a reactive esterified OH group, this is preferably alkylsulphonyloxy having 1–6 carbon atoms (preferably methylsulphonyloxy) or arylsulphonyloxy having 6–10 carbon atoms (preferably phenyl- or p-tolylsulphonyloxy, or furthermore also 2-naphthalenesulphonyloxy).

The compounds of the formula I can preferably be obtained by reacting compounds of the formula II with compounds of the formula III.

If desired, the starting materials can also be formed in situ, so that they are not isolated from the reaction mixture but are immediately reacted further to give the compounds of the formula I.

On the other hand, it is possible to carry out the reaction in stages.

The starting materials of the formulae II and III are generally known. If they are not known, they can be prepared by methods known per se. Compounds of the formula II can be obtained, for example, by reacting $POCl_3$ with the corresponding hydroxypyrimidines which are synthesized from thiophene derivatives and CN-substituted alkylenecarboxylic esters (Eur. J. Med. Chem. 23, 453 (1988)). The hydroxypyrimldlnes are prepared either by dehydrogenation of the corresponding tetrahydrobenzothienopyrimidine compounds, or after the cyclization of 2-aminobenzothiophene-3-carboxylic acid derivatives with aldehydes or nitriles which is customary for preparing pyrimidine derivatives (for example Houben-Weyl E9b/2).

Specifically, the reaction of the compounds of the formula II with the compounds of the formula III is carried out in the presence or absence of an inert solvent at temperatures between about −20 and about 150°, preferably between 20 and 100°.

The addition of an acid-binding agent, for example an alkyl metal hydroxide, carbonate or bicarbonate or alkaline earth metal hydroxide, carbonate or bicarbonate, or of another alkali metal or alkaline earth metal, preferably potassium, sodium or calcium, salt of a weak acid, or the addition of an organic base, such as triethylamine, dimethylamine, pyridine or quinoline, or of an excess of the amine component may be favourable.

Suitable inert solvents are, For example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methylglycol or ethylglycol), ethylene glycol dimethyl ether (diglyme); ketones, such as acetone or butanone; amides, such as acetamide, dimethylacetamide, N-methylpyrrolidone or dimethylformamide (DMF); nitrites, such as acetonitrile; sulphoxides, such as dimethyl sulphoxide (DMSO); nitro compounds, such as nitromethane or nitrobenzene; esters, such as ethyl acetate, or mixtures of the solvents mentioned.

It is furthermore possible to convert a radical X in a compound of the formula I into another radical X, for example by hydrolysing an ester or a cyano group to give a COOH group. Ester groups can be hydrolysed, for example, using NaOH or KOH in water, water/THF or water/dioxane, at temperatures between 0 and 100°. Carboxylic acids can be converted with, for example, thionyl chloride into the corresponding carbonyl chlorides, and these can be converted into carboxamides. By dehydration in a known manner, these give carbonitriles.

An acid of the formula I can be converted into the associated acid addition salt using a base, for example by reaction of equivalent amounts of the acid and the base in an inert solvent, such as ethanol, and subsequent evaporation. Possible bases for this reaction are, in particular, those which give physiologically acceptable salts. The acid of the formula I can thus be converted with a base (for example sodium hydroxide or carbonate or potassium hydroxide or carbonate) into the corresponding metal salt, in particular alkalis metal salt or alkalne earth metal salt, or into the corresponding ammonium salt. Possible bases for this reaction are, in particular, also those organic bases which give physiologically acceptable salts, such as, for example, ethanolamine.

On the other hand, a base of the formula I can be converted into the associated acid addition salt using an acid, for example by reaction of equivalent amounts of the base and the acid in an inert solvent, such as ethanol, and subsequent evaporation. Acids which are suitable for this reaction are, in particular, those which give physiologically acceptable salts. It is thus possible to use inorganic acids, for example sulphuric acid, nitric acid, hydrohalic acids, such as hydrochloric acid or hydrobromic acid, phosphoric acids, such as orthophosphoric acid, sulphaminic acid, furthermore organic acids, in particular aliphatic, alicyclic, araliphatic, aromatic or heterocyclic mono- or polybasic carboxylic, sulphonic or sulphuric acids, for example formic acid, acetic acid, propionic acid, pivalic acid, diethylacetic acid, malonic acid, succinnic acid, pimelic acid, fumaric acid, maleic acid, lactic acid, tartaric acid, malic acid, citric acid, gluconic acid, ascorbic acid, nicotinic acid, isonicotinic acid, methane- or ethanesulphonic acid, ethanedisulphonic acid, 2-hydroxyethanesulphonic acid, benzenesulphonic acid, p-toluenesulphonic acid, naphthalene-mono- and disulphonic acids and laurylsulphuric acid. Salts with physiologically unacceptable acids, for example picrates, can be used for isolation and/or purification of the compounds of the formula I.

The invention furthermore provides the use of the compounds of the formula I and/or their physiologically acceptable salts for the preparation of pharmaceutical formulations, in particular by a non-chemical route. For this use, they can brought into a suitable dosage form together with at least one solid, liquid and/or semi-liquid carrier or auxiliary, and if appropriate in combination with one or more further active compounds.

The invention also provides medicaments of the formula I and their physiologically acceptable salts as phosphodiesterase V-inhibitors.

The invention furthermore provides pharmaceutical formulations comprising at least one compound of the formula I and/or one of its physiologically acceptable salts.

These Formulations can be used as medicaments in human or veterinary medicine. Possible carriers are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, and furthermore suspensions, emulsions or implants are used for parenteral administration, and ointments, creams or powders are used for topical application. The novel compounds can also be lyophilized and the resulting lyophilizates can be used, for example, for the preparation of injection preparations. The formulations a mentioned can be sterilized and/or comprise auxiliaries, such as lubricants, preservatives, stabilizers and/or wetting agents, emulsifiers, salts for influencing the osmotic pressure, buffer substances, colorants, flavourings and/or several other active compounds, for example one or more vitamins.

The compounds of the formula I and their physiologically acceptable salts can be employed for combating diseases with which an increase in the cGMP(cyclic guanosine monophosohate) level leads to an inhibition or prevention of inflammation and to muscular relaxation. The compounds according to the invention can be used in particular in the treatment of diseases of the cardiovascular system and for the treatment and/or therapy of impaired potency.

For these uses, the substances are generally preferably administered in dosages of between 1 and 500 mg, in particular between 5 and 100 mg per dosage unit. The daily dosage is preferably between about 0.02 and 10 mg/kg of body weight. However, the specific dose for each patient depends on the most diverse factors, for example on the activity of the specific compound employed, on the age, body weight, general state of health, sex, on the diet, on the administration time and route, on the rate of elimination, medicament combination and severity of the particular disease to which the therapy applies. Oral administration is preferred.

All the temperatures above and below are stated in 0° C. In the following examples, "customary work-up" means: water is added, if required, the pH is adjusted to between 2 and 10, if required, depending on the constitution of the end product, the mixture is extracted with ethyl acetate or dichloromethane, the organic phase is separated off, dried over sodium sulphate and evaporated and the residue is purified by chromatography over silica gel and/or by crystallization.

Mass spectrometry (MS): EI (electron impact ionization) $M^+$; FAB (fast atom bombardment) $(M+H)^+$.

EXAMPLE 1

Methyl 3-(4-chlorobenzothieno[2,3-d]pyrimidin-2-yl) propionate [obtainable by cyclization of methyl 2-amino-5, 6,7,8-tetrahydrobenzothiophene-3-carboxylate with methyl 3-cyanopropionate, dehydrogenation with sulphur and subsequent chlorination with phosphorus oxychloride/ dimethylamine] and 3-chloro-4-methoxybenzylamine ("A") in N-methylpyrrolidone are stirred at 110° for 5 hours. The solvent is removed and the residue is worked up as usual. This gives methyl 3-[4-(3-chloro-4-methoxybenzylamino) benzothieno[2,3-d]pyrimidin-2-yl]propionate as a colourless oil.

Similarly, reaction of "A"

with methyl 2-(4-chlorobenzothieno[2,3-d]pyrimidin-2-yl)acetate gives methyl 2-[4-(3-chloro-4-methoxybenzylamino) benzothieno[2,3-d]pyrimidin-2-yl]acetate.

Similarly, reaction of 3,4-methylenedioxybenzylamine with methyl 3-(4-chlorobenzothieno[2,3-d]pyrimidin-2-yl)propionate gives methyl 3-[4-(3,4-methylenedioxybenzylamino) benzothieno[2,3-d]pyrimidin-2-yl]propionate.

Similarly, reaction of "A"

with methyl 4-(4-chlorobenzothieno[2,3-d]pyrimidin-2-yl)butyrate gives methyl 4-[4-(3-chloro-4-methoxybenzylamino) benzothieno[2,3-d]pyrimidin-2-yl]butyrate.

Similarly, reaction of 3,4-methylenedioxybenzylamine with methyl 4-(4-chlorobenzothieno[2,3-d]pyrimidin-2-yl)butyrate gives methyl 4-[4-(3,4-methylenedioxybenzylamino) benzothieno[2,3-d]pyrimidin-2-yl]butyrate.

Similarly, reaction of "A"

with methyl 5-(4-chlorobenzothieno[2,3-d]pyrimidin-2-yl)valerate gives methyl 5-[4-(3-chloro-4-methoxybenzylamino) benzothieno[2,3-d]pyrimidin-2-yl]valerate.

Similarly, reaction of 3,4-methylenedioxybenzylamine with methyl 5-(4-chlorobenzothieno[2,3-d]pyrimidin-2-yl)valerate gives methyl 5-[4-(3,4-methylenedioxybenzylamino) benzothieno[2,3-d]pyrimidin-2-yl]valerate.

Similarly, reaction of "A"

with methyl 7-(4-chlorobenzothieno[2,3-d]pyrimidin-2-yl)heptanoate gives methyl 7-[4-(3-chloro-4-methoxybenzylamino) benzothieno[2,3-d]pyrimidin-2-yl]heptanoate.

Similarly, reaction of 3,4-methylenedioxybenzylamine with methyl 7-(4-chlorobenzothieno[2,3-d]pyrimidin-2-yl)heptanoate gives
methyl 7-[4-(3,4-methylenedioxybenzylamino)benzothieno[2,3-d]pyrimidin-2-yl]heptanoate.

Similarly, reaction of "A"
with methyl 2-[4-(4-chlorobenzothieno[2,3-d]pyrimidin-2-yl)cyclohex-1-yl]acetate gives
methyl 2-{4-[4-(3-chloro-4-methoxybenzylamino)benzothieno[2,3-d]pyrimidin-2-yl]cyclohex-1-yl}acetate.

Similarly, reaction of 3,4-methylenedioxybenzylamine with methyl 2-[4-(4-chlorobenzothieno[2,3-d]pyrimidin-2-yl)cyclohex-1-yl]acetate gives
methyl 2-{4-[4-(3,4-methylenedioxybenzylamino)benzothieno[2,3-d]pyrimidin-2-yl]cyclohex-1-yl}acetate.

Similarly, reaction of benzylamine
with methyl 3-(4-chlorobenzothieno[2,3-d]pyrimidin-2-yl)propionate gives
methyl 3-(4-benzylaminobenzothieno[2,3-d]pyrimidin-2-yl)propionate;
with methyl 4-(4-chloroberzothieno[2,3-d]pyrimidin-2-yl)butyrate gives
methyl 4-(4-benzylaminobenzothieno[2,3-d]pyrimidin-2-yl)butyrate;
with methyl 5-(4-chlorobenzothieno[2,3-d]pyrimidin-2-yl)valerate gives
methyl 5-(4-benzylaminobenzothieno[2,3-d]pyrimidin-2-yl)valerate.

Similarly, reaction of "A"
with methyl 4-(4-chlorobenzothieno[2,3-d]pyrimidin-2-yl)cyclohexanecarboxylate gives
methyl 4-[4-(3-chloro-4-methoxybenzylamino)benzothieno[2,3-d]pyrimidin-2-yl]cyclohexanecarboxylate and by reaction of 3,4-methylenedioxybenzylamine gives
methyl 4-[4-(3,4-methylenedloxybenzylamino)benzothieno[2,3-d]pyrimidin-2-yl]cyclohexanecarboxylate.

EXAMPLE 2

Methyl 3-[4-(3-chloro-4-methoxybenzylamino)-benzothieno[2,3-d]pyrimidin-2-yl]propionate is dissolved in ethylene glycol monomethyl ether and; after addition of 32% strength NaOH, stirred at 110° for 5 hours. 20% strength HCl is added, and the mixture is then extracted with dichloromethane. Addition of petroleum ether affords 3-[4-(3-chloro-4-methoxybenzylamino)benzothieno[2,3-d]pyrimidin-2-yl]propionic acid, m.p. 218°.

The precipitated crystals are dissolved in isopropanol and admixed with ethanolamine. Crystallization gives 3-[4-(3-chloro-4-methoxybenzylamino)benzothieno[2,3-d]pyrimidin-2-yl]propionic acid, ethanolamine salt.

The compounds
4-[4-(3-chloro-4-methoxybenzylamino)benzothieno[2,3-d]pyrimidin-2-yl]butyric acid, m.p. 225°; ethanolamine salt m.p. 150°;
5-[4-(3-chloro-4-methoxybenzylamino)benzothieno[2,3-d]pyrimidin-2-yl]valeric acid, m.p. 210°; ethanolamine salt m.p. 141°;
4-[4-(3,4-methylenedioxybenzylamino)benzothieno[2,3-d]pyrimidin-2-yl]butyric acid, hydrochloride, m.p. 245° are obtained similarly.

Similarly, the esters listed under Example 1 give the following carboxylic acids:

2-[4-(3-chloro-4-methoxybenzylamino)benzothieno[2,3-d]pyrimidin-2-yl]acetic acid,
3-[4-(3,4-methylenedioxybenzylamino)benzothieno[2,3-d]pyrimidin-2-yl]propionic acid,
5-[4-(3,4-methylenedioxybenzylamino)benzothieno[2,3-d]pyrimidin-2-yl]valeric acid,
7-[4-(3-chloro-4-methoxybenzylamino)benzothieno[2,3-d]pyrimidin-2-yl]heptanoic acid,
7-[4-(3,4-methylenedioxybenzylamino)benzothieno[2,3-d]pyrimidin-2-yl]heptanoic acid,
2-{4-[4-(3-chloro-4-methoxybenzylamino)benzothieno[2,3-d]pyrimidin-2-yl]cyclohex-1-yl}acetic acid,
2-{4-[4-(3,4-methylenedioxybenzylamino)benzothieno[2,3-d]pyrimidin-2-yl]cyclohex-1-yl}acetic acid,
3-(4-benzylaminobenzothieno[2,3-d]pyrimidin-2-yl) propionic acid,
4-(4-benzylaminobenzothieno[2,3-d]pyrimidin-2-yl) butyric acid,
5-(4-benzylaminobenzothieno[2,3-d]pyrimidin-2-yl) valeric acid,
4-[4-(3-chloro-4-methoxybenzylamino)benzothieno[2,3-d]pyrimidin-2-yl]cyclohexanecarboxylic acid, ethanolamine salt m.p. 167°;
4-[4-(3,4-methylenedioxybenzylamino)benzothieno[2,3-d]pyrimidin-2-yl]cyclohexanecarboxylic acid, ethanolamine salt m.p. 143.

EXAMPLE 3

A mixture of 1.5 g of methyl 4-(4-chlorobenzothieno)[2,3-d]pyrimidin-2-yl)phenylcarboxylate ("B"), prepared by dehydrogenation of the corresponding 5,6,7,8-tetrahydrobenzothieno[2,3-d]pyrimidine compound with sulphur and subsequent chlorination with phosphorus oxychloride/dimethylamine, and 1.5 g of 3-chloro-4-methoxybenzylamine in 20 ml of N-methylpyrrolidone is heated at 110° fox 4 hours. After cooling, the mixture is worked up as usual. This gives 2.6 g of methyl 4-[4-(3-chloro-4-methoxybenzylamino)-[1]benzothieno[2,3-d]pyrimidin-2-yl]benzoate, m.p. 203–204°.

Similarly to Example 2, 1.2 g of the ester give 1.0 g of
4-[4-(3-chloro-4-methoxybenzylamino)-[1]benzothieno-[2,3-d]pyrimidin-2-yl]benzoic acid, ethanolamine salt, m.p. 189–190°.
Similarly to Example 1, "B" and 3,4-methylenedioxybenzylamine give
methyl 4-[4-(3,4-methylenedioxybenzylamino)-[1]benzothieno[2,3-d]pyrimidin-2-yl]benzoate and this affords, by ester hydrolysis, 4-[4-(3,4-methylenedioxybenzylamino)-[1]benzothieno-[2,3-d]pyrimidin-2-yl]benzoic acid, sodium salt, m.p. >260°.
The compounds
4-[4-(3-chloro-4-methoxybenzylamino)-[1]benzothieno[2,3-d]pyrimidin-2-yl]phenylacetic acid, ethanolamine salt, m.p. 130° and
4-[4-(3,4-methylenedioxybenzylamino)-[1]benzothieno[2,3-d]pyrimidin-2-yl]phenylacetic acid, ethanolamine salt M.p. 202°, are obtained.

EXAMPLE 4

1 equivalent of 3-[4-(3-chloro-4-methoxybenzylamino)benzothieno[2,3-d]pyrimidin-2-yl]propionic acid and 1.2 equivalents of thionyl chloride are stirred in dichloromethane for 2 hours. The solvent is removed, affording 3-[4-(3-chloro-4-methoxybenzylamino)benzothieno[2,3-d]
pyrimidin-2-yl]propionyl chloride.

The residue is transferred into aqueous ammonia and stirred for one hour, giving, after customary work-up, 3-[4-(3-chloro-4-methoxybenzylamino)benzothieno[2,3-d]pyrimidin-2-yl]propionamide.

EXAMPLE 5

At 0°, 1 equivalent of DMF and 1 equivalent of oxalyl chloride are dissolved in acetonitrile. 1 equivalent of 3-[4-(3-chloro-4-methoxybenzylamino)-benzothieno[2,3-d]pyrimidin-2-yl]propionamide is then added. The mixture is stirred for one hour. Customary work-up gives 3-[4-(3-chloro-4-methoxybenzylamino)benzothieno[2,3-d]pyrimidin-2-yl]propionitrile.

EXAMPLE 6

Similarly to Examples 1, 2 and 3, reaction of the corresponding chloropyrimidine derivatives with 3,4-ethylenedioxybenzylamine gives the carboxylic acids below;

- 4-[4-(3,4-ethylenedioxybenzylamino)benzothieno[2,3-d]pyrimidin-2-yl]butyric acid,
- 3-[4-(3,4-ethylenedioxybenzylamino)benzothieno[2,3-d]pyrimidin-2-yl]propionic acid,
- 5-[4-(3,4-ethylenedioxybenzylamino)benzothieno[2,3-d]pyrimidin-2-yl]valeric acid,
- 7-[4-(3,4-ethylenedioxybenzylamino)benzothieno[2,3-d]pyrimidin-2-yl]heptanoic acid,
- 2-{4-[4-(3,4-ethylenedioxybenzylamino)benzothieno[2,3-d]pyrimidin-2-yl]cyclohex-1-yl}acetic acid,
- 4-[4-(3,4-ethylenedioxybenzylamino)benzothieno[2,3-d]pyrimidin-2-yl]cyclohexanecarboxylic acid,
- 4-[4-(3,4-ethylenedioxybenzylamino)-[1]benzothieno[2,3-d]pyrimidin-2-yl]benzoic acid, decomp. 220–230°;
- 4-[4-(3,4-ethylenedioxybenzylamino)-[1]benzothieno[2,3-d]pyrimidin-2-yl]benzoic acid, ethanolamine salt m.p. 252;
- 4-[4-(3,4-ethylenedioxybenzylamino)-[1]benzothieno[2,3-d]pyrimidin-2-yl]phenylacetic acid.

Similarly, reaction with 3,4-dichlorobenzylamine gives the compounds below;

- 4-[4-(3,4-dichlorobenzylamino)benzothieno[2,3-d]pyrimidin-2-yl]butyric acid,
- 3-[4-(3,4-dichlorobenzylamino)benzothieno[2,3-d]pyrimidin-2-yl]propionic acid,
- 5-[4-(3,4-dichlorobenzylamino)benzothieno[2,3-d]pyrimidin-2-yl]valeric acid,ethanolamine salt m.p. 160°;
- 7-[4-(3,4-dichlorobenzylamino)benzothieno[2,3-d]pyrimidin-2-yl]heptanoic acid,
- 2-{4-[4-(3,4-dichlorobenzylamino)benzothieno[2,3-d]pyrimidin-2-yl]cyclohex-1-yl}acetic acid,
- 4-[4-(3,4-dichlorobenzylamino)benzothieno[2,3-d]pyrimidin-2-yl]cyclohexanecarboxylic acid,
- 4-[4-(3,4-dichlorobenzylamino)-[1]benzothieno[2,3-d]pyrimidin-2-yl]benzoic acid,
- 4-[4-(3,4-dichlorobenzylamino)-[1]benzothieno[2,3-d]pyrimidin-2-yl]phenylacetic aced.

Similarly, reaction with 3-chloro-4-ethoxybenzylamine gives the compounds below;

- 4-[4-(3-chloro-4-ethoxybenzylamino)benzothieno[2,3-d]pyrimidin-2-yl]butyric acid,
- 3-[4-(3-chloro-4-ethoxybenzylamino)benzothieno[2,3-d]pyrimidin-2-yl]propionic acid,
- 5-[4-(3-chloro-4-ethoxybenzylamino)benzothieno[2,3-d]pyrimidin-2-yl]valeric acid,
- 7-[4-(3-chloro-4-ethoxybenzylamino)benzothieno[2,3-d]pyrimidin-2-yl]heptanoic acid,
- 2-{4-[4-(3-chloro-4-ethoxybenzylamino)benzothieno[2,3-d]pyrimidin-2-yl]cyclohex-1-yl}acetic acid,
- 4-[4-(3-chloro-4-ethoxybenzylamino)benzothieno[2,3-d]pyrimidin-2-yl]cyclohexanecarboxylic acid,
- 4-[4-(3-chloro-4-ethoxybenzylamino)-[1]benzothieno[2,3-d]pyrimidin-2-yl]benzoic acid, m.p. 185–187°;
- 4-[4-(3-chloro-4-ethoxybenzylamino)-[1]benzothieno[2,3-d]pyrimidin-2-yl]phenylacetic acid.

Similarly, reaction with 3-chloro-4-isopropoxybenzylamine gives the compounds below;

- 4-[4-(3-chloro-4-isopropoxybenzylamino)benzothieno[2,3-d]pyrimidin-2-yl]butyric acid,
- 3-[4-(3-chloro-4-isopropoxybenzylamino)benzothieno[2,3-d]pyrimidin-2-yl]propionic acid,
- 5-[4-(3-chloro-4-isopropoxybenzylamino)benzothieno[2,3-d]pyrimidin-2-yl]valeric acid, ethanolamine salt m.p. 130°;
- 7-[4-(3-chloro-4-isopropoxybenzylamino)benzothieno[2,3-d]pyrimidin-2-yl]heptanoic acid,
- 2-{4-[4-(3-chloro-4-isopropoxybenzylamino)benzothieno-[2,3-d]pyrimidin-2-yl]cyclohex-1-yl}acetic acid,
- 4-[4-(3-chloro-4-isopropoxybenzylamino)benzothieno[2,3-d]pyrimidin-2-yl]cyclohexanecarboxylic acid,
- 4-[4-(3-chloro-4-isopropoxybenzylamino)-[1]benzothieno-[2,3-d]pyrimidin-2-yl]benzoic acid, m.p. 240–241°;
- 4-[4-(3-chloro-4-isopropoxybenzylamino)-[1]benzothieno-[2,3-d]pyrimidin-2-yl]phenylacetic acid.

The following examples relate to pharmaceutical formulations:

EXAMPLE A

Injection Vials

A solution of 100 g of an active compound of the formula i and 5 g of disodium hydrogen phosphate in 3 l of doubly distilled water is brought to pH 6.5 with 2N hydrochloric acid, and subjected to sterile filtration and injection vials are filled with this solution, lyophilized under sterile conditions and closed under sterile conditions. Each injection vial contains 5 mg of active compound.

EXAMPLE B

Suppositories

A mixture of 20 g of an active compound of the formula I with 100 g of soyalecithin and 1400 g of cacao butter is melted, poured into moulds and allowed to cool. Each suppository comprises 20 mg of active compound.

EXAMPLE C

Solution

A solution of 1 g of an active compound of the formula I, 9.38 g of $NaH_2PO_4.2\,H_2O$, 28.48 g of $Na_2HPO_4.12\,H_2O$ and 0.1 g of benzalkonium chloride in 940 ml of doubly distilled water is prepared. The pH is brought to 6.8 and the solution is topped up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed to tablets in the customary manner such that each tablet comprises 10 mg of active compound.

EXAMPLE F

Coated Tablets

Tablets are pressed analogously to Example E and are then covered in the customary manner with a coating of sucrose, potato starch, talc, tragacanth and dyestuff.

EXAMPLE G

Capsules

Hard gelatin capsules are filled with 2 kg of active compound of the formula I in the customary manner such that each capsule contains 20 mg of the active compound.

EXAMPLE H

Ampoules

A solution of 1 kg of active compound of the formula I in 60 l of doubly distilled water is subjected to sterile filtration and ampoules are filled with the solution, lyophilized under sterile conditions and closed under sterile-conditions. Each ampoule contains 10 mg of active compound.

EXAMPLE I

Spray for Inhalation 14 g of active compound of the formula I are dissolved in 10 l of isotonic NaCl solution and commercially available spray vessels with a sump mechanism are filled with the solution. The solution can be sprayed into the mouth or nose. One spray puff (about 0.1 ml) corresponds to a dose of about 0.14 mg.

What is claimed is:

1. Compounds of the formula I

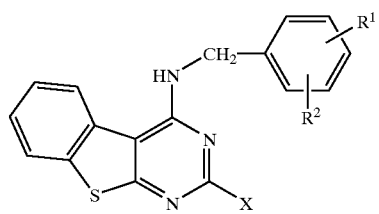

I in which $R^1$, $R^2$ independently of one another are each H, A, OA or Hal, $R^1$ and $R^2$ together are also alkylene having 3–5 carbon atoms, —O—$CH_2$—$CH_2$—, —$CH_2$—O—$CH_2$—, —O—$CH_2$—O— or —O—$CH_2$—$CH_2$—O—, X is $R^5$, $R^6$ or $R^4$ which is monosubstituted by $R^7$, $R^4$ is linear or branched alkylene having 1–10 carbon atoms, in which one or two $CH_2$ groups may be replaced by —CH=CH— groups, $R^5$ is cycloalkyl or cycloalkylalkylene having 5–12 carbon atoms, $R^6$ is phenyl or phenylmethyl, $R^7$ is COOH, COOA, $CONH_2$, CONHA, $CON(A)_2$ or CN, A is alkyl having 1 to 6 carbon atoms and Hal is F, Cl, Br or I, and their physiologically acceptable salts.

2. A compound of the formula I according to claim 1, which is:

(a) 3-[4-(3-chloro-4-methoxybenzylamino) benzo-[4,5]thieno[2,3-d]pyrimidin-2-yl]propionic acid;

(b) 4-[4-(3,4-methylenedioxybenzylamino) benzo-[4,5]thieno [2,3-d]pyrimidin-2-yl]butyric acid;

(c) 7-[4-(3,4-methylenedioxybenzylamino) benzo-[4,5]thieno [2,3-d]pyrimidin-2-yl]heptanoic acid;

(d) 7-[4-(3-chloro-4-methoxybenzylamino) benzo[4,5]-thieno[2,3-d]pyrimidin-2-yl]heptanoic acid;

(e) 5-[4-(3-chloro-4-methoxybenzylamino) benzo[4,5]-thieno[2,3-d]pyrimidin-2-yl]valeric acid;

(f) 2-{4-[4-(3-chloro-4-methoxybenzylamino) benzo-[4,5]thieno[2,3-d]pyrimidin-2-yl]cyclohex-1-yl}acetic acid;

(g) 4-[4-(3,4-methylenedioxybenzylamino)benzo[4,5]-thieno[2,3-d]pyrimidin-2-yl]cyclohexanecarboxylic acid;

(h) 4-[4-(3,4-methylenedioxybenzylamino)benzo[4,5]-thieno[2,3-d]pyrimidin-2-yl]benzoic acid;

(i) 4-[4-(3,4-methylenedioxybenzylamino)benzo[4,5]-thieno[2,3-d]pyrimidin-2-yl]phenylacetic acid; or (j) 4-[4-(3-chloro-4-methoxybenzylamino) benzothieno[2,3-d]pyrimidin-2-yl]cyclohexanecarboxylic acid;

or a physiologically acceptable salt thereof.

3. A process for preparing a compound of the formula I according to claim 1, or a salt thereof comprising:

a) reacting a compound of the formula II

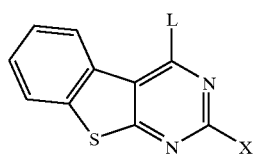

II in which

X is as defined above and L is Cl, Br, OH, SCH$_3$, or a reactive esterified OH group;

with a compound of the formula III

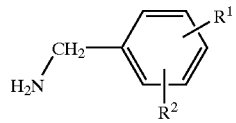

in which R$^1$ and R$^2$ are as defined above, and, optionally, b) converting an ester radical X in a compound of the formula I into a COOH radical by hydrolysing an ester radical to a COOH radical or converting a COOH radical into an amide or a cyano radical; and, further optionally, converting a compound of the formula I into one of its physiologically acceptable salts.

4. Process for the preparation of pharmaceutical formulations, characterized in that a compound of the formula I according to claim 1 and/or one of its physiologically acceptable salts is brought into a suitable dosage form together with at least one solid, liquid or semi-liquid carrier or auxiliary.

5. A pharmaceutical formulation, which comprises at least one compound of the formula I according to claim 1 and/or one of its physiologically acceptable salts and at least one solid, liquid or semi-liquid carrier or auxiliary.

6. Compounds of the formula I according to claim 1 and their physiologically acceptable salts for combating diseases of the cardiovascular system and for the treatment and/or therapy of impaired potency.

7. Medicaments of the formula I according to claim 1 and their physiologically acceptable salts as phosphodiesterase V-inhibitors.

8. A method for treating a disease of the cardiovascular system or treating impaired sexual potency which comprises administering to a patient an effective amount of a compound of the formula I of claim 1 and/or a physiologically acceptable salt thereof.

9. The method of claim 8, wherein the disease is a cardiovascular disease.

10. The method of claim 8, wherein the disease is impaired sexual potency.

11. The method of claim 9, wherein the compound of the formula I and/or physiologically acceptable salt thereof is administered in a daily dosage of 0.02 to 10 mg/kg of body weight of a patient.

12. The method of claim 10, wherein the compound of the formula I and/or physiologically acceptable salt thereof is administered in a daily dosage of 0.02 to 10 mg/kg of body weight of a patient.

13. The formulation of claim 5, wherein the compound of the formula I and/or physiologically acceptable salt thereof is provided in a dosage of 1 to 500 mg in the formulation.

14. A compound of claim 1, wherein X is phenyl, phenylmethyl or R$^4$ which is substituted by COOH, COOA, CONH$_2$, CON(A)$_2$, CONHA or CN.

15. A compound of claim 1, wherein R$^1$ and R$^2$ together are alkylene having 3–5 carbon atoms, —O—CH$_2$—CH$_2$—, —O—CH$_2$—O— or —O—CH$_2$—CH$_2$—O— and X is phenyl, phenylmethyl or R$^4$ which is substituted by COOH, COOA, CONH$_2$, CON(A)$_2$, CONHA or CN.

16. A compound of claim 1, wherein R$^1$ and R$^2$ are independently of one another H, A, OA or Hal, or R$^1$ and R$^2$ together are alkylene having 3–5 carbon atoms, —O—CH$_2$—CH$_2$—, —O—CH$_2$—O— or —O—CH$_2$—CH$_2$—O— and X is phenyl, phenylmethyl or R$^4$ which is substituted by COOH, COOA, CONH$_2$, CON(A)$_2$, CONHA or CN.

17. A compound of claim 1, wherein R$^1$ and R$^2$ are independently of one another H, A, OA or Hal, or R$^1$ and R$^2$ together are alkylene having 3–5 carbon atoms, —O—CH$_2$—CH$_2$—, —O—CH$_2$—O— or —O—CH$_2$—CH$_2$—O—, X is cyclohexyl, phenyl, phenylmethyl or alkylene of 2–5 carbon atoms which is monosubstituted by R$^7$, and R$^7$ is COOH or COOA.

18. The method of claim 3, wherein L is a reactive esterified OH group which is alkylsulphonyloxy of 1–6 carbon atoms or arylsulphonyloxy of 6–10 carbon atoms.

* * * * *